United States Patent [19]
Palumbo et al.

[11] Patent Number: 5,728,084
[45] Date of Patent: Mar. 17, 1998

[54] ABSORBENT ARTICLE WITH CONTROLLED DISTRIBUTION OF LIQUID

[75] Inventors: Gianfranco Palumbo, Pescara; Giovanni Carlucci, Chieti; Luigi Marinelli; Remo Di Girolamo, both of Pescara; Michael Divo, Teatino, all of Italy

[73] Assignee: The Proctor & Gamble Company, Cincinnati, Ohio

[21] Appl. No.: 392,844

[22] PCT Filed: Sep. 13, 1996

[86] PCT No.: PCT/US93/08598
§ 371 Date: Jun. 2, 1995
§ 102(e) Date: Jun. 2, 1995

[87] PCT Pub. No.: WO94/06385
PCT Pub. Date: Mar. 31, 1994

[30] Foreign Application Priority Data

Sep. 16, 1992 [IT] Italy ................. TO92A0761

[51] Int. Cl.⁶ ................. A61F 13/17; A61F 13/20
[52] U.S. Cl. ................. 604/378; 604/379; 604/370; 604/368; 604/372
[58] Field of Search ................. 604/358, 372, 604/368, 378, 379, 385.1, 366, 370

[56] References Cited

U.S. PATENT DOCUMENTS

| | | |
|---|---|---|
| Re. 26,515 | 1/1969 | Holliday et al. . |
| Re. 32,649 | 4/1988 | Brandt et al. . |
| 1,946,626 | 2/1934 | Jurgensen . |
| 2,296,341 | 9/1942 | Fourness . |
| 2,548,341 | 4/1951 | Bricmont . |
| 2,551,663 | 5/1951 | Fox . |
| 2,929,179 | 3/1960 | George . |
| 2,952,259 | 9/1960 | Burgeni ................. 604/380 |
| 3,095,878 | 7/1963 | Bassett . |
| 3,343,543 | 9/1967 | Glassman . |
| 3,356,092 | 12/1967 | Joa . |
| 3,386,442 | 6/1968 | Sabee . |
| 3,397,697 | 8/1968 | Rickard . |
| 3,406,688 | 10/1968 | Cubitt . |
| 3,431,911 | 3/1969 | Meisel . |
| 3,523,535 | 8/1970 | Croon et al. . |
| 3,528,421 | 9/1970 | Vaillancourt et al. . |
| 3,572,342 | 3/1971 | Lindquist et al. . |
| 3,604,422 | 9/1971 | Sabee . |

(List continued on next page.)

FOREIGN PATENT DOCUMENTS

| | | |
|---|---|---|
| 0158914 | 10/1985 | European Pat. Off. ............. 604/358 |
| 254 476 | 1/1988 | European Pat. Off. . |
| 0 339 461 | 11/1989 | European Pat. Off. . |
| 0 343 941 | 11/1989 | European Pat. Off. . |
| 391 814 A2 | 4/1990 | European Pat. Off. . |
| 0 397 110 A2 | 11/1990 | European Pat. Off. . |
| 0 399 564 A | 11/1990 | European Pat. Off. . |
| 0 414 541 | 2/1991 | European Pat. Off. . |
| 0 443 627 A2 | 8/1991 | European Pat. Off. . |
| 3917791 | 12/1990 | Germany . |
| 2 078 527 | 1/1962 | United Kingdom . |
| WO 90/14813 | 12/1990 | WIPO . |
| WO 91/11162 | 8/1991 | WIPO . |
| WO 91/11163 | 8/1991 | WIPO . |
| WO 91/11164 | 8/1991 | WIPO . |
| WO 91/11165 | 8/1991 | WIPO . |

*Primary Examiner*—John G. Weiss
*Assistant Examiner*—P. Zuttarelli
*Attorney, Agent, or Firm*—Edward J. Milbrada; Jeffrey V. Bamber; Steven W. Miller

[57] ABSTRACT

A disposable sanitary towel (1) comprising a liquid-permeable upper layer (5), an impermeable lower layer (7) and an absorbent element (6), is provided with an intermediate layer (10) disposed between the upper layer (5) and the absorbent element (6) and extending around the side edges (8) of the absorbent element (6) such that it can distribute the liquid received and prevent losses of liquid from the side edges of the absorbent element (6). The towel (1) is further provided with an absorbent element (6) comprising an improved layer structure.

20 Claims, 10 Drawing Sheets

U.S. PATENT DOCUMENTS

| | | |
|---|---|---|
| 3,651,809 | 3/1972 | Champaigne, Jr. . |
| 3,695,269 | 10/1972 | Malaney . |
| 3,716,430 | 2/1973 | Croon et al. . |
| 3,736,931 | 6/1973 | Glassman . |
| 3,799,167 | 3/1974 | Miller et al. . |
| 3,815,602 | 6/1974 | Johns et al. . |
| 3,825,006 | 7/1974 | Ralph . |
| 3,838,693 | 10/1974 | Sherman . |
| 3,844,288 | 10/1974 | Kiela . |
| 3,871,037 | 3/1975 | Willington . |
| 3,954,721 | 5/1976 | Gross . |
| 3,983,095 | 9/1976 | Bashaw et al. . |
| 3,996,936 | 12/1976 | Widlund et al. . |
| 4,050,462 | 9/1977 | Woon et al. . |
| 4,136,697 | 1/1979 | Smith . |
| 4,211,227 | 7/1980 | Anderson et al. . |
| 4,212,302 | 7/1980 | Karami ............................ 604/368 |
| 4,231,357 | 11/1980 | Hessner . |
| 4,285,342 | 8/1981 | Mesek . |
| 4,287,251 | 9/1981 | King et al. . |
| 4,324,246 | 4/1982 | Mullane et al. . |
| 4,335,722 | 6/1982 | Jackson . |
| 4,338,371 | 7/1982 | Dawn et al. . |
| 4,360,022 | 11/1982 | Usami et al. . |
| 4,364,992 | 12/1982 | Ito et al. . |
| 4,397,644 | 8/1983 | Matthews et al. . |
| 4,410,324 | 10/1983 | Sabee . |
| 4,411,660 | 10/1983 | Dawn et al. ...................... 604/368 |
| 4,500,315 | 2/1985 | Pieniak et al. . |
| 4,501,586 | 2/1985 | Holtman . |
| 4,536,181 | 8/1985 | Cook . |
| 4,537,590 | 8/1985 | Peiniak et al. . |
| 4,557,777 | 12/1985 | Sabee . |
| 4,579,556 | 4/1986 | McFarland . |
| 4,610,678 | 9/1986 | Weisman et al. . |
| 4,655,757 | 4/1987 | McFarland et al. . |
| 4,666,439 | 5/1987 | Williams et al. . |
| 4,673,402 | 6/1987 | Weisman et al. . |
| 4,676,784 | 6/1987 | Erdman et al. . |
| 4,681,577 | 7/1987 | Stern et al. . |
| 4,685,914 | 8/1987 | Holtman . |
| 4,699,823 | 10/1987 | Kellenberger et al. . |
| 4,701,177 | 10/1987 | Ellis et al. . |
| 4,762,520 | 8/1988 | Wallstrom . |
| 4,769,022 | 9/1988 | Chang et al. . |
| 4,781,711 | 11/1988 | Houghton et al. . |
| 4,787,896 | 11/1988 | Houghton et al. . |
| 4,798,603 | 1/1989 | Meyer et al. ...................... 604/378 |
| 4,855,179 | 8/1989 | Bourland et al. . |
| 4,880,419 | 11/1989 | Ness . |
| 4,888,238 | 12/1989 | Katz et al. . |
| 4,900,318 | 2/1990 | Toth . |
| 4,923,454 | 5/1990 | Seymour et al. . |
| 4,935,022 | 6/1990 | Lash et al. . |
| 4,938,754 | 7/1990 | Mesek . |
| 4,950,262 | 8/1990 | Takagi . |
| 4,963,139 | 10/1990 | Dabroski . |
| 4,988,344 | 1/1991 | Reising et al. . |
| 4,988,345 | 1/1991 | Reising . |
| 4,990,147 | 2/1991 | Freeland . |
| 5,009,650 | 4/1991 | Bernadin . |
| 5,013,309 | 5/1991 | Baigas, Jr. et al. . |
| 5,037,409 | 8/1991 | Chen et al. . |
| 5,061,259 | 10/1991 | Goldman et al. . |
| 5,061,260 | 10/1991 | Callahan et al. . |
| 5,098,422 | 3/1992 | Davis et al. . |
| 5,135,521 | 8/1992 | Luceri et al. ...................... 604/383 |
| 5,147,345 | 9/1992 | Young et al. . |
| 5,149,335 | 9/1992 | Kellenberger et al. . |
| 5,175,046 | 12/1992 | Nguyen . |
| 5,176,668 | 1/1993 | Bernadin . |
| 5,192,606 | 3/1993 | Proxmire et al. . |
| 5,200,248 | 4/1993 | Thompson et al. . |
| 5,217,445 | 6/1993 | Young et al. . |
| 5,300,054 | 4/1994 | Feist et al. . |
| 5,304,161 | 4/1994 | Noel et al. . |
| 5,360,420 | 11/1994 | Cook et al. . |
| 5,364,382 | 11/1994 | Latimer et al. . |

ABSORBENT ARTICLE WITH CONTROLLED DISTRIBUTION OF LIQUID

BACKGROUND OF INVENTION

The present invention relates to a sanitary towel generally consisting of an upper layer which is permeable to liquids, a lower layer which is impermeable to liquids and an absorbent element disposed between them.

More particularly, the invention relates to a sanitary towel the structure of which comprises one or more layers intended to control the distribution of the liquid which is deposited on the surface of the upper layer facing the user's body.

Preferred arrangements of the invention comprise an absorbent element which contains hydrogelling absorbent material as a component, and preferably as the principal component.

Sanitary towels having an upper layer which is permeable to liquids, an impermeable lower layer and an absorbent element which is disposed between them and contains hydrogelling absorbent material are known in the prior art.

The patent U.S. Pat. No. 5,009,653 describes a sanitary towel comprising an upper layer which is permeable to liquids, a lower layer which is impermeable to liquids and an absorbent element disposed between them, the absorbent element consisting of a layered structure consisting of two dry-formed external tissue layers and of a central layer of hydrogelling absorbent material.

A layer for collecting the liquid, consisting of a non-woven fabric, 70% of which is composed of rayon and 30% of which is composed of polyester fibres, is disposed between the upper layer and the absorbent element and is intended to improve the sideways distribution of the liquid passing through the upper layer. The sideways distribution of the liquid in the collecting layer increases the surface area of the absorbent element to which the released liquid can have access, but, on the other hand, it is possible for the liquid to migrate to the edges of the sanitary towel such that it can spot and stain the user's underclothes in certain conditions of use.

The patent EP-A-257280 describes a composite covering layer for an absorbent article, such as a sanitary towel, in which a substantially hydrophobic perforated polymer film which is less than 0.762 mm thick and has a total open area of at least 35% is disposed on a layer of non-woven fabric secured thereto, the openings in the first layer having dimensions which are insufficient to allow the passage of a 1% saline solution under the effect of gravity alone, whilst the second layer has a capillary structure such that it allows a rise of less than 12.7 mm of 1% saline solution after 15 minutes.

The absorbent article comprises an absorbent element having a two-layered composite structure, in particular a low-density upper layer formed of cellulosic fibres and a lower layer consisting of a high-density mixture of cellulose fibres and superabsorbent material.

The lower side of the absorbent element is secured to a polyethylene sheet which extends to the side edges of the absorbent element to prevent the fluid being able to pass from the base and side edges of the absorbent element to the user's underclothes.

It should be noted that the composite covering layer enables the liquid to flow in a single direction to ensure improved properties with respect to the backflow of liquid, and it is further noted that the said layer displays very poor diffusion properties, or a low ability for transmitting the liquid in a sideways direction.

The present invention seeks to avoid the disadvantages of an intermediate layer which is completely permeable to liquids, at the same time retaining the ability to distribute the liquid received to zones of the absorbent element remote from the area where it is collected.

OBJECT OF INVENTION

It is therefore an object of the invention to produce a sanitary towel having a layered structure which enables the liquid released over the surface of the said sanitary towel facing the users body to be controlled.

It is also an object of the invention to produce a sanitary towel having an absorbent element disposed between a lower layer which is impermeable to liquids and an upper layer which is permeable to liquids and onto which the liquid is released, in which an intermediate layer disposed between the upper layer and the absorbent layer distributes the released liquid over the surface of the absorbent element facing the user's body, however it is arranged such that losses of liquid from the side edges of the towel towards the user's underclothes are prevented.

It is a further object of the invention to produce a sanitary towel in which an intermediate layer disposed between the upper layer and the absorbent element distributes the liquid released onto the surface facing the body of the user of the absorbent element, the intermediate element extending around the side edges of the absorbent element, at least at its central portion so as to enable the liquid to be diffused, at least along the internal surface of the intermediate layer, around the longitudinal side edges of the absorbent element, the intermediate layer furthermore being arranged such that losses of liquid from the side edges of the absorbent element towards the user's underclothes are prevented.

It is an even further object of the invention to produce a sanitary towel having an upper layer which is permeable to liquids, a lower layer which is impermeable to liquids and an absorbent layer comprised between them, the sanitary towel further comprising a hydrophilic intermediate layer disposed between the upper layer and the absorbent element, in which the absorbent element comprises a layered structure in which the density of the respective layers decreases from the upper layer to the lower layer.

In accordance with the present invention, these objects are achieved with a sanitary towel having the characteristics specifically mentioned in the following claims.

A sanitary towel according to the present invention is characterized in that the absorbent element is covered on its surface facing the user's body and along its side edges with an intermediate layer which comprises a part which is substantially impermeable to liquids, at the side edges of the absorbent element, and a part substantially permeable to liquids, on at least a pan of the surface of the absorbent element facing the user's body.

Preferably, the sanitary towel according to the present invention comprises an intermediate layer having a bulk of more than 5 $cm^3/g$, a capillary diffusion capacity of less than 150 seconds in the "horizontal diffusion test", and an absorption capacity of less than 1 g in the "free absorption test".

Preferably, the sanitary towel according to the present invention comprises an absorbent element formed of a first, a second and a third fibrous layer, the first fibrous layer having a greater density than that of the second fibrous layer and the third fibrous layer having a lower density than that of the first and second fibrous layers.

BRIEF DESCRIPTION OF THE DRAWINGS

The invention will now be described purely by way of non-limiting example with reference to the appended drawings, in which.

DETAILED DESCRIPTION OF THE INVENTION

The present invention relates to disposable absorbent articles and more particularly to ladies'sanitary towels which are worn in direct contact with the body externally of the user's vulvar region, which can absorb body fluids, and which are subsequently disposed of after a single use.

The present invention is not, however, restricted simply to sanitary towels but also applies to other disposable absorbent articles, such as, for example, so-called panty liners and the like.

Figure 1:
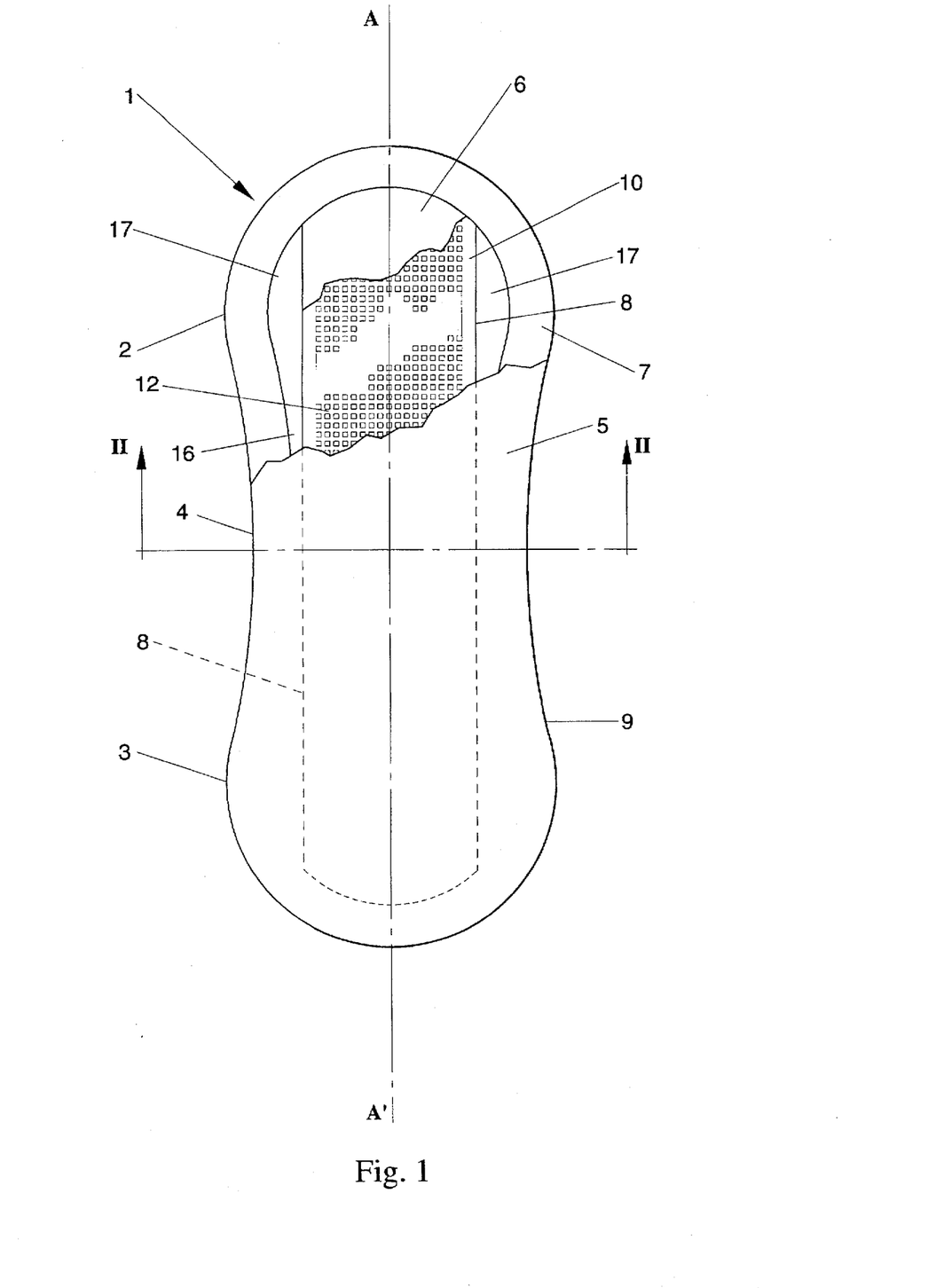
FIG. 1 is a plan view of a sanitary towel produced according to the present invention, viewed from its side which is to face the user.
Figure 2:
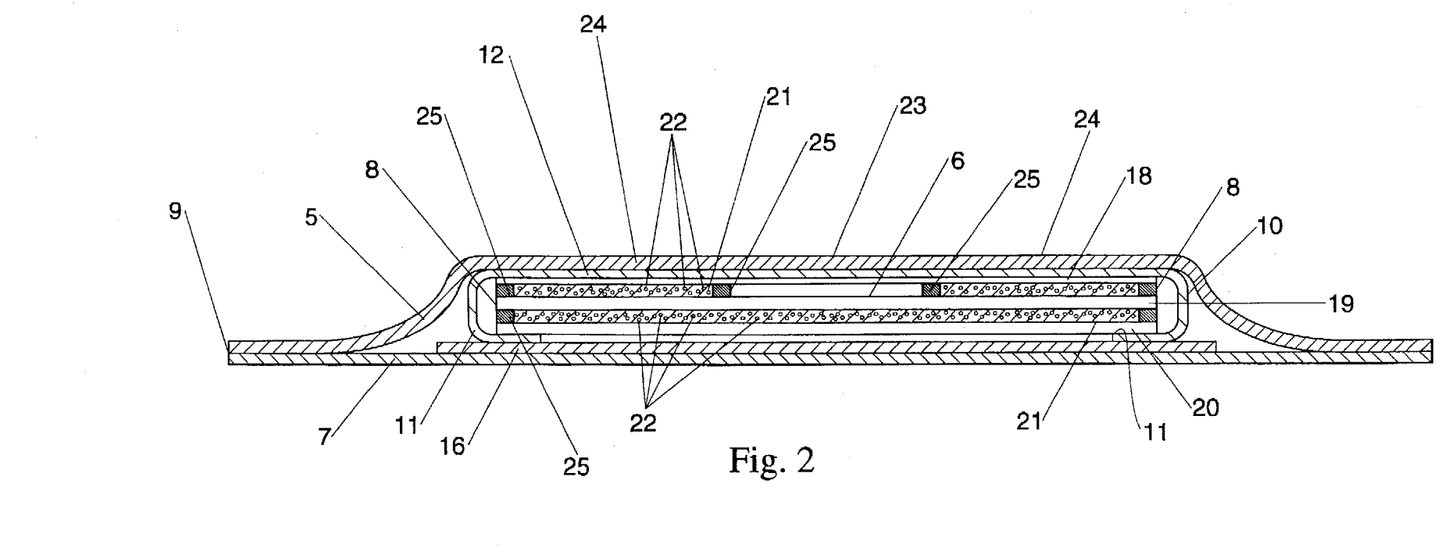
FIG. 2 is a view in section of the towel along the line II—II in FIG. 1.

The disposable sanitary towel illustrated in FIGS. 1 and 2 represents a preferred embodiment of an absorbent article produced according to the present invention.

FIG. 1 illustrates a sanitary towel 1, produced according to the present invention with a portion of the structure removed to show the construction more clearly; in particular it shows the upper side of the towel which, in use, is in direct contact with the user's body.

FIG. 1 shows a front region 2, a rear region 3 and a central region 4 comprised between them; there is further shown a longitudinal axis AA' and a transverse axis corresponding to the sectional line II—II.

The towel comprises an upper layer 5 which is permeable to liquids and which is to contact the user's body directly, an absorbent element 6, and a lower layer 7 which is impermeable to liquids.

In the arrangement illustrated, the towel is shaped such that it has a greater width at the from region 2 and the rear region 3, with the result that it is narrower in the central region 4; as is known, this shape permits improved adaptability to the user's anatomy; the absorbent element 6 is rectangular with rounded ends and with straight longitudinal side edges 8 which are parallel to one another, and is characterized by a width which is slightly smaller with respect to the minimum width of the towel in correspondence with the central zone 4.

The liquid-permeable upper layer 5 and the impermeable lower layer 7 are the same shape and size as the external shape of the whole absorbent product and are joined to each other, for example by means of a glued or heat-sealed line, along at least the outer contour 9 of the towel.

The liquid-permeable upper layer 5 should enable the liquid to pass quickly through its thickness towards the structure below; it can be produced in various ways known from the prior art, for example from non-woven fabric, however, a perforated polymeric film which is permeable to liquids but is not absorbent is preferred.

In a preferred arrangement of the present invention, the surface of the permeable upper layer 5 facing the users body is hydrophilic, particularly in the case in which the upper layer 5, is produced with a perforated polymer film.

The hydrophilic surface ensures a quicker passage of the liquid through the upper layer 5, towards the underlying absorbent structure and also reduces the possibility of some of the liquid itself running over the surface of the upper layer.

The surface of the permeable upper layer 5 facing the body can be rendered hydrophilic by treatment with a surfactant, applied for example by spraying or by means of a roller.

Alternatively, the surfactant can be incorporated directly into the material from which the permeable upper layer 5, is formed.

The absorbent element 6 is covered by an intermediate layer 10 which covers the surface facing the user's body and, at least in the central region 4 of the towel 1, the longitudinal side edges 8 of the absorbent element 6 by means of the two longitudinal marginal portions 11; as illustrated in FIG. 2, the intermediate layer 10 preferably comprises longitudinal marginal portions 11 of a width such that they also extend partially in correspondence with the side of the absorbent element facing the underclothing.

The intermediate layer 10 is substantially impermeable to liquids in the longitudinal marginal portions 11 which wrap around the longitudinal side edges 8 and at least part of the surface, facing the underclothing, of the absorbent element 6, and comprises a portion 12 which is substantially permeable to liquids on at least pan of the surface of the absorbent element 6 facing the user's body.

The intermediate layer 10 is characterized by high bulkiness, greater than 5 cm³/g, and preferably good capillary diffusion of the liquid and a low absorption capacity.

The capillary diffusion capacity and the absorption capacity of the material constituting the intermediate layer are assessed by means of a "Horizontal diffusion test" and a "Free absorption test", both performed on rectangular samples of material which are 80 mm long and 25.4 mm wide, using a 0.9% by weight saline solution.

For each test, the values obtained represent the average of the values measured for three equivalent samples.

Horizontal Diffusion Test

An apparatus is used which is known as a "Demand wettability tester", illustrated in "Absorbency", edited by Pronoy K. Chatterjee and published by Elsevier Science Publishers B.V., ed. 1985, page 62, with reference to B. M. Lichstein, "INDA Technical Symposium," U.S.A., 1974, page 129.

The test is performed by placing on the horizontal test plate a sample of material having the agreed dimensions with one end at level with the hole through which the liquid is released with a hydrostatic head of approximately zero.

The time taken by the liquid to reach the other end of the sample covering the distance of 80 mm is measured in seconds.

Free Absorption Test

The sample with the agreed dimensions is weighed and then placed carefully on the surface of the liquid; the surface of the material facing the surface of the liquid is the surface of use.

The sample is left on the liquid for 1 minute, is then raised at one end with forceps, is left to drip for one minute and is finally weighed again.

The difference between the initial weight and the final weight represents the amount of liquid absorbed freely by the sample being tested.

The material constituting the intermediate layer 10 should have a capillary diffusion time, measured according to the "Horizontal diffusion test", of less than 150 seconds and a free absorption capacity, measured according to the "Free absorption test" of less than 1 g, and preferably of less than 0.5 g.

The use of the covering structure for sanitary hygiene products, described in the EP-B-207904 in the name of the same Applicants, rendered hydrophilic by means of suitable treatment, has proved particularly preferable.

Figure 3:
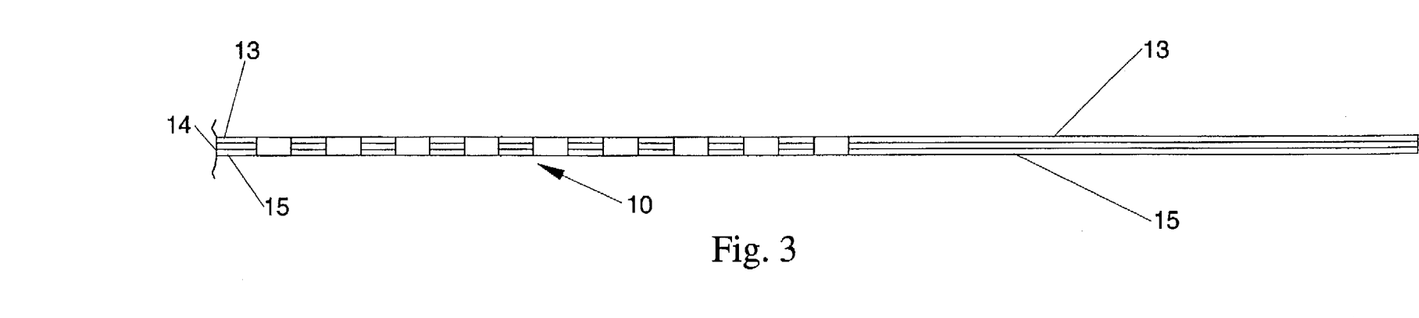
FIG. 3 is a view in partial section of a preferred arrangement of the intermediate layer comprised in the towel according to the present invention.

The structure, illustrated in particular in FIG. 3, is generally perforated and comprises an upper layer 13 consisting of a non-woven fabric, an intermediate layer 14 consisting of a polymeric film and a lower layer 15 consisting of a non-woven fabric; the three layers are combined together to form a structure having a thickness of between 200μ and 700μ.

In a preferred embodiment of the present invention, the fibres constituting the non-woven fabric of the upper layer 13 and lower layer 15 of the layered structure constituting the intermediate layer 10 are of the hydrophilic type, for example rendered such by means of suitable treatment with surfactants before the structure itself is formed; in addition, the entire structure is perforated and thus rendered permeable to liquids, only in the portion 12 of the intermediate layer 10, whilst the longitudinal marginal portions 11 covering the longitudinal side edges 8 and at least part of the surface, facing the underclothing, of the absorbent element 6, are not perforated and are thus substantially impermeable.

In use, the structure can receive and transmit the liquid quickly through the holes in the permeable portion 12, from the permeable overlying upper structure 5 to the underlying absorbent element 6.

The high bulkiness of the intermediate layer 10 isolates the permeable upper structure 5 from the surface of the absorbent element 6, helping to keep the surface of the towel facing the user's body dry during use.

The unperforated longitudinal marginal portions 11 of the intermediate layer 10 prevent losses of liquid which might occasionally occur at the longitudinal side edges 8 of the absorbent element 6, when the sanitary towel is subject to the normal pressures of use.

The capillary diffusion capacity of the upper fibrous layer 13 and lower fibrous layer 15, together with the low liquid absorption capacity, are such that some of the liquid received through the overlying upper layer 5 is transmitted by capillarity to the interior of the fibrous layers remote from the zone in which the liquid itself is initially received, typically in the centre of the permeable portion 12, being diffused both in the longitudinal and in the transverse directions.

In this way, the surface area of the intermediate structure 10 through which the liquid passes towards the underlying absorbent element 6 is increased, with the advantage of a greater extent of the absorbent element being involved in the absorption of the liquid.

In addition, the liquid migrating along the intermediate layer 10 in the transverse direction is conveyed beyond the side longitudinal edges 8 of the absorbent element 6 until it reaches the lower surface of the absorbent element 6, at least as far as where the longitudinal marginal portions 11 of the intermediate layer 10 extend below the absorbent element 6.

Thus, some of the liquid can also be absorbed through the lower surface of the absorbent element 6.

The liquid preferably advances along the surface of the intermediate layer 10, internally facing the absorbent element 6, corresponding, in the preferred embodiment, to the lower fibrous layer 15 of the layered structure in FIG. 3, since it arrives there both by internal capillary action through the fibres and by the absorbent element 6, for example because of possible losses from the longitudinal side edges 8.

The low liquid absorption capacity of the material of which the intermediate layer 10 is composed is such that only a minimum amount of liquid is retained inside the structure, the greater part, on the other hand, being conveyed to the absorbent element 6 by the method described.

A lower, stopping layer 16 is preferably comprised between the absorbent element 6, possibly partially enveloped by the intermediate layer 10 in correspondence with the surface facing the underclothing, and the impermeable lower layer 7.

As FIG. 1 shows, the lower, stopping layer 16 preferably has the same shape as the sanitary towel 1 and thus, at the front zone 2 and the rear zone 3, it is wider than the rectangular absorbent element 6, forming four portions 17.

The lower, stopping layer 16 is preferably hydrophobic and has a very low capillary diffusion capacity; in a preferred arrangement, the layer is formed of the same perforated layered structure which constitutes the intermediate layer 10, with the fibres of the fibrous layers 13 and 15 being hydrophobic instead of hydrophilic.

Small amounts of liquid which may be absorbed by the absorbent element 6 and successively released during use from the lower face facing the underclothing, or migrating at the base along the external surface of the intermediate layer 10, can be received by the lower, stopping layer 16 inside the small cavities constituted by holes and retained there without being able to diffuse anywhere else by virtue of the hydrophobic nature of the fibres of which the layer is composed.

In addition, the four portions 17 of the lower, stopping layer 16 which, at the front region 2 and rear region 3 of the shaped towel 1, extend sideways relative to the longitudinal side edges of the rectangular absorbent element 6, and provide the sanitary towel 1 with greater consistency and thickness in the zones.

The absorbent element 6 can be produced from a large variety of absorbent materials commonly used in sanitary towels, babies' nappies and other disposable-type absorbent articles.

Suitable materials may be cellulose fibres obtained from wood pulp, absorbent foams or sponges, synthetic fibres, hydrogelling absorbent materials or any material or combinations of equivalent materials.

Hydrogelling absorbent materials, commonly known as superabsorbents, are polymers which can swell up and absorb large quantities of liquid, particularly water, or also, to a lesser extent, body fluid They also have the particular property that they retain the fluids even under moderate pressure; owing to this characteristic, their use in combination with hydrophilic fibres for disposable absorbent articles has been proposed for some time.

The high absorption capacity of superabsorbents is not, however, combined with similarly rapid absorption and this may adversely affect the performance of absorbent articles incorporating these substances.

In fact, superabsorbents may give rise to a phenomenon defined, in the prior art, as "gel blocking": when a particle of superabsorbent is in contact with the liquid, its external surface starts to absorb the liquid and swells up, obstructing the transmission of the liquid into the particle itself; the liquid can penetrate further into the still-dry core of the particle only by means of a very slow diffusion mechanism.

This phenomenon may prevent full use being made of the large absorption capacities of superabsorbent substances.

In any case, with the use of hydrogelling absorbent materials, it is possible to produce absorbent elements which contain fewer hydrophilic fibres for a given absorption capacity and which consequently are characterized by smaller dimensions, particularly thicknesses than conventional absorbent elements made of fibres alone Structures have been formed in which the fibres and the particles of hydrogelling, absorbent material are disposed in separate, superposed layers, generally characterized by a greatly reduced thickness.

A thin, layered absorbent structure such as the one described in patent application TO92A000566 of 3rd Jul. 1992 is particularly preferred as an absorbent element for the sanitary towel of the present invention.

The above absorbent structure is formed of two or more fibrous layers and, between each pair of the fibrous layers, there is an intermediate layer comprising particles of hydrogelling absorbent material and particles of thermoplastic polymeric organic material; the fibrous layers extend sideways beyond the respective intermediate layers, forming longitudinal marginal portions.

The fibrous layers, comprising between them the respective intermediate layers, are joined together by melting of the particles of thermoplastic organic material and by means of continuous lines of adhesive extending longitudinally, at least in correspondence with each longitudinal marginal portion.

The absorbent element 6, illustrated in FIG. 2, is a preferred arrangement of the thin layered absorbent structure described.

The absorbent element is composed of a first fibrous layer 18, a second fibrous layer 19 and a third fibrous layer 20, and of two intermediate layers 21 comprising a mixture of particles 22 of hydrogelling absorbent material and thermoplastic polymeric organic material.

The surface distribution of the particles 22 forming the intermediate layers 21 may be non-uniform, in particular, in the example described in the patent application EP 92306824.1 of 27th Jul. 1992, the absorbent element 6 may comprise a central longitudinal collection zone 23 and two side zones 24 positioned between the collection zone 23 and the longitudinal side edges 8, with a lower concentration of the hydrogelling absorbent material, comprised in the intermediate layers 21, in the longitudinal central collection zone 23 than in the two side zones 24.

In the preferred embodiment illustrated in FIG. 2, the first intermediate layer 21, between the first and second fibrous layers 18 and 19 respectively, comprises the central longitudinal collection zone 23 in which the particles 22 are distributed at a lower surface density with respect to the remaining part of the intermediate structure itself and with respect to the entire second intermediate layer 21 comprised between the second and third fibrous layers 19 and 20, respectively.

In the preferred arrangement illustrated in FIG. 2, the longitudinal central collection zone 23 is completely free from particles 22.

FIG. 2 also shows continuous lines of adhesive 25 which extend longitudinally both along the longitudinal marginal portions of the layered structure, located, in the arrangement illustrated, at the longitudinal side edges 8 of the absorbent element 6, and along the edges of the longitudinal central collection zone 23.

The fibrous layers composing the layered absorbent structure illustrated in FIG. 2 are not equal to one another: in particular, the density of the layers decreases progressively from the first fibrous layer to the third.

Preferably, the first and second fibrous layers 18 and 19 respectively consist of dry formed ("air laid") layers of short cellulose fibres, whilst the lower fibrous layer 20 is formed of cellulose fibres and synthetic fibres and is thermally stabilised ("thermobonded"); the presence of the synthetic fibres provides the layer with elasticity and bulk.

In use, the more dense upper layers 18 and 19 receive the liquid and can transmit it quickly towards the underlying layers of fibres and hydrogelling absorbent materials, at the same time distributing it longitudinally and transversely so as to increase the area of the underlying layers involved in absorption. The longitudinal central zone 23, without hydrogelling absorbent material, comprised in the first intermediate layer 21, permits quicker collection of the liquid which, at least in this zone, is thus transmitted quickly and directly from the first fibrous layer 18 to the second layer 19.

Being more bulky, the lower fibrous layer 20 has a lower diffusion capacity but can take in a greater quantity of liquid, thus contributing to the overall absorption capacity of the entire absorbent element 6 together with the particles of hydrogelling absorbent material of the intermediate layers 21.

Furthermore, by virtue of the elasticity provided by the presence of synthetic fibres, it does not tend to collapse when it is wet; small amounts of liquid which can escape from the lower fibrous layer 20 when the absorbent is subject to normal pressures of use can, however, be reabsorbed by the particles of hydrogelling absorbent material of the overlying intermediate layer 21.

The following FIGS. 4 to 11 illustrate some alternative arrangements for a sanitary towel produced according to the present invention, the elements common thereto being indicated with the same numerals used in FIGS. 1 and 2.

Figure 4:
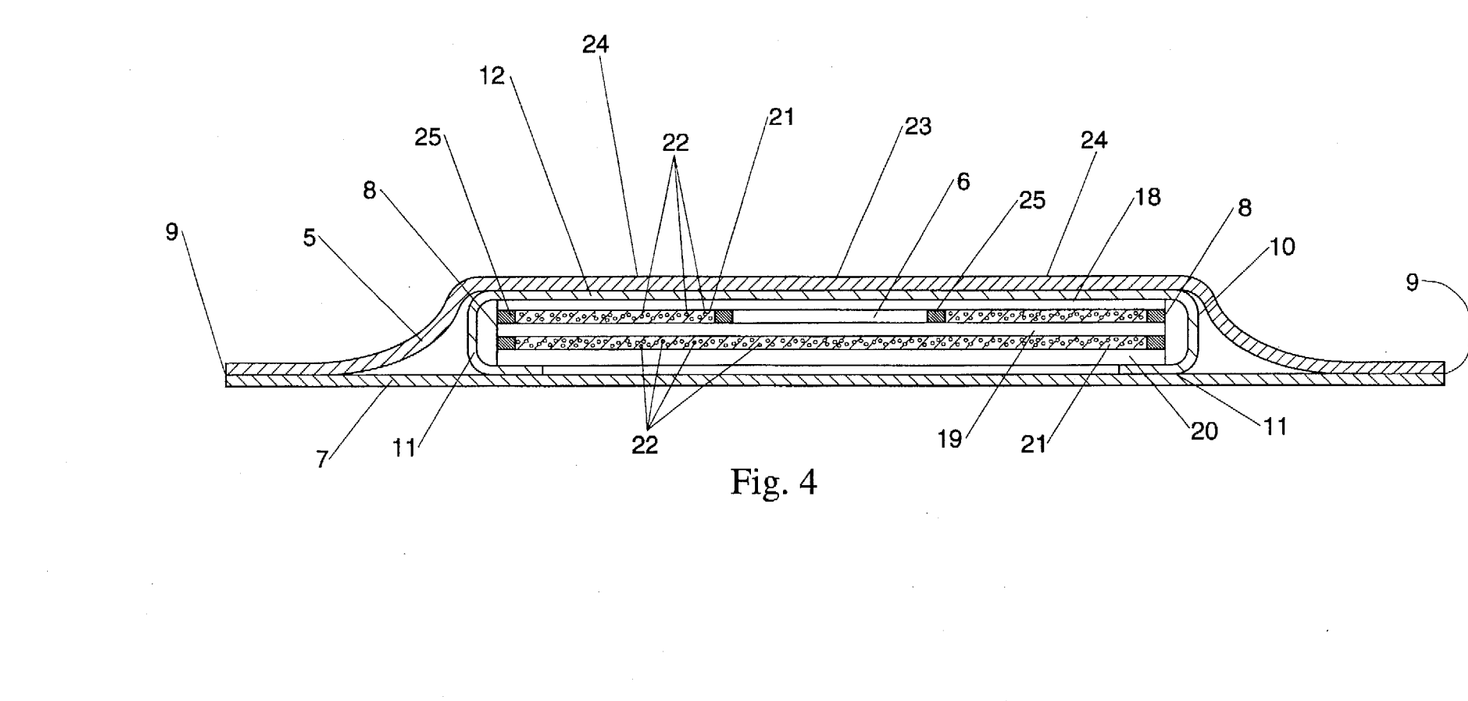
FIGS. 4 and 5 are views in section of two alternative arrangements of a towel according to the present invention.
Figure 5:
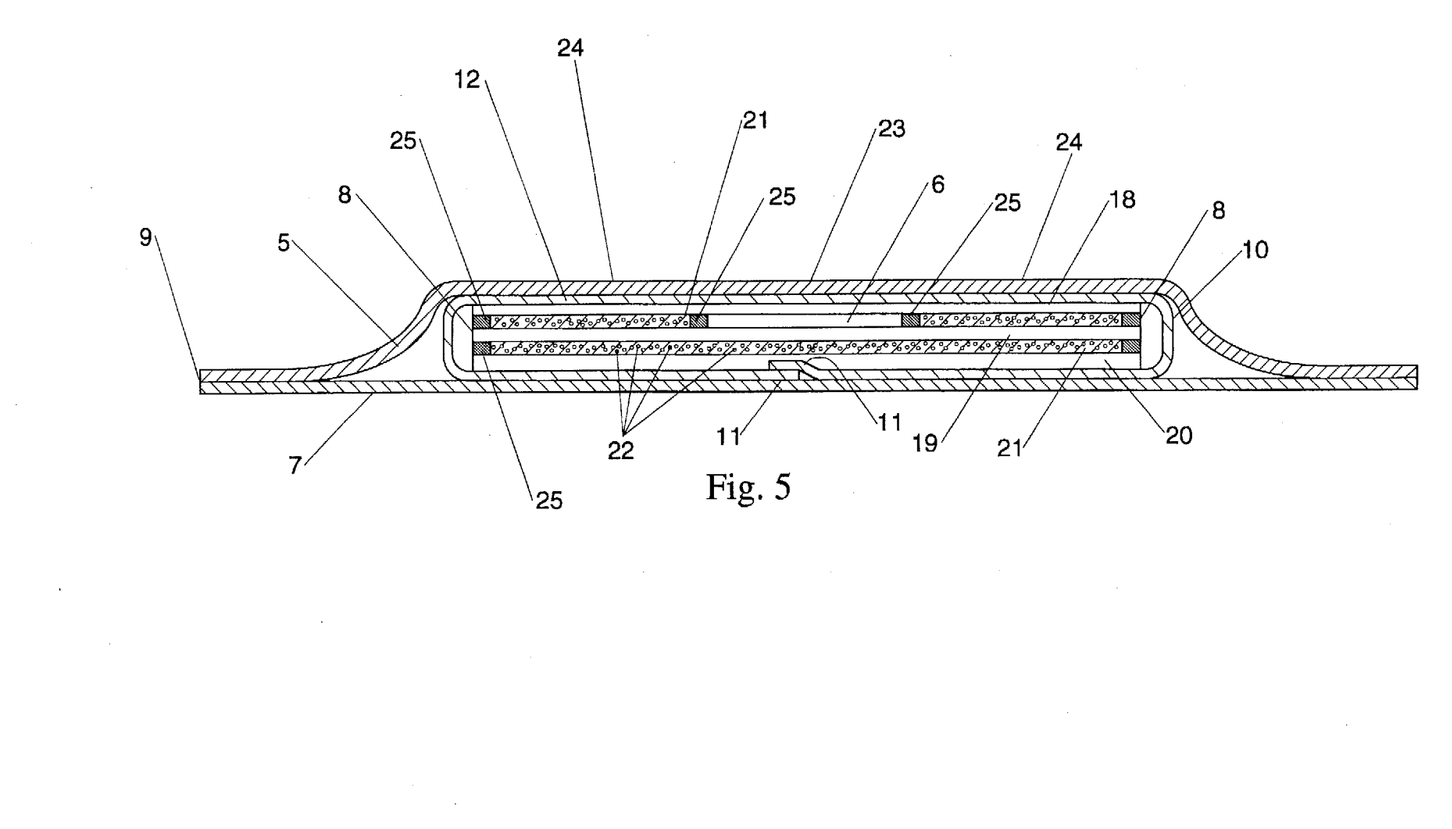

FIGS. 4 and 5 illustrate two alternative arrangements for the sanitary towel of the present invention which both differ from the preferred arrangement in FIG. 2 by the lack of the lower stopping layer 16.

In addition, in the arrangement in FIG. 5, the intermediate structure 10 is completely wrapped around the absorbent element 6, with the longitudinal marginal portions 11 partially overlapping the underside of the absorbent element for increased protection against possible losses of liquid from the base of the absorbent element itself.

FIG. 6 illustrates some alternative arrangements for an absorbent element 6, which is to be incorporated in a sanitary towel produced in accordance with the present invention, in which the absorbent element is produced from a layered absorbent structure formed by two fibrous layers, one upper layer 26 and one lower layer 27, with the interposition of an intermediate layer 21 comprising hydrogelling absorbent material and comprising continuous lines of adhesive 25 at least at the longitudinal side edges.

Figure 6A:
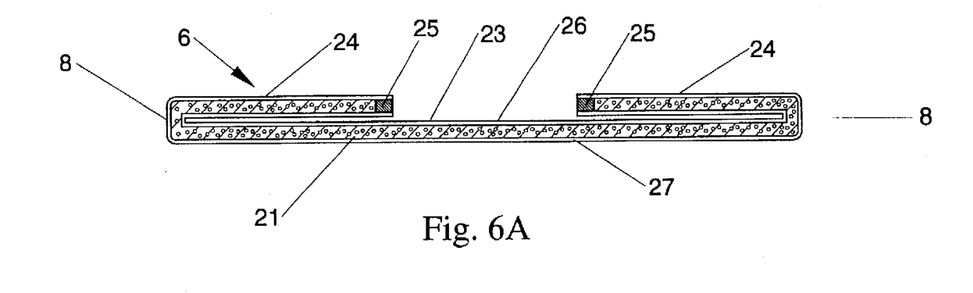
FIG. 6 is a view in section of three alternative arrangements for the single absorbent element incorporated in the sanitary towel according to the present invention.
Figure 6B:
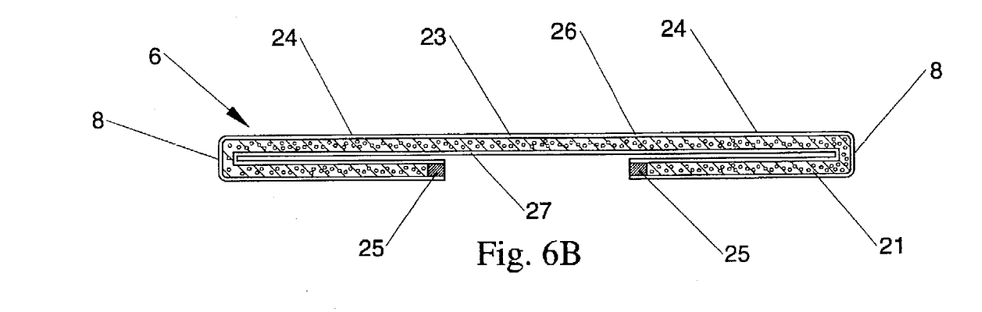
Figure 6C:
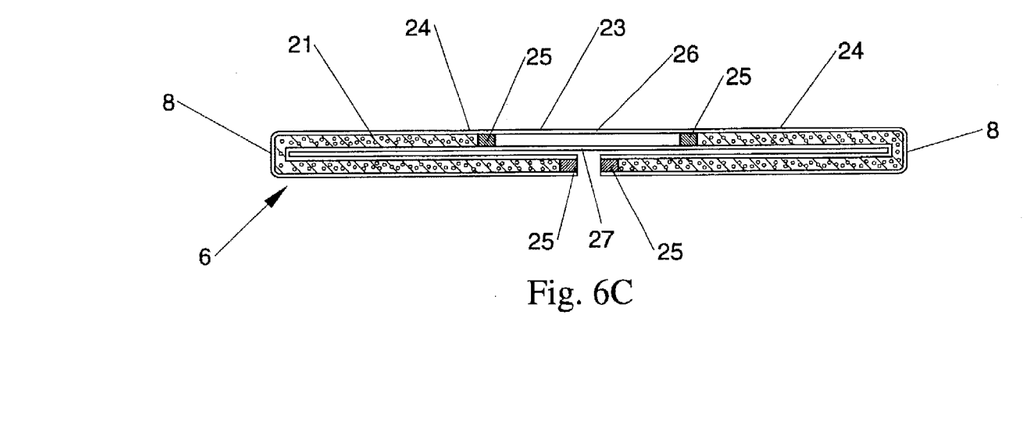

The initial layered absorbent structure is wider than the resultant absorbent element 6 which is obtained by the folding back onto themselves of the two longitudinal ends of the layered structure at the top, as shown in 6a, or at the bottom, as shown in 6b and 6c.

In all three drawings, the resultant absorbent elements show a longitudinal collection zone 23, longitudinal side edges 8 and two side zones 24 positioned between the collection zone 23 and the side edge 8.

In arrangements 6a and 6b, the side zones 24, characterized by the presence of a greater amount of hydrogelling absorbent material, are produced from two overlapping layers of the same layered absorbent structure, whilst the collection zone corresponds to the central portion of the absorbent element 6 characterized by the presence of a single layer of the layered absorbent structure.

In arrangement 6c, the longitudinal ends folded back under the layered absorbent structure are extended such that they almost touch one another along the respective longitudinal edges, generally along the longitudinal axis of the absorbent element itself; the longitudinal central collection zone 23 is such that it comprises a zone without any hydrogelling absorbent material inside the intermediate layer 21, which is also defined by the lines of adhesive 25.

The two fibrous layers composing the layered absorbent structure in FIGS. 6a, 6b and 6c can have various densities, with the upper layer 26 being more dense than the lower layer 27.

In a more preferred manner, the upper fibrous layer 26 consists of a dry-formed ("air laid") layer of short cellulose fibres, whilst the lower fibrous layer 27 is formed of cellulose fibres and thermally stabilised ("thermobonded") synthetic fibres.

Layered absorbent structures of the type equivalent to those described can, however, be produced in different ways, for example by combining and superposing fibrous layers having different widths, possible with the interposition of intermediate layers comprising hydrogelling absorbent material.

Figure 7:
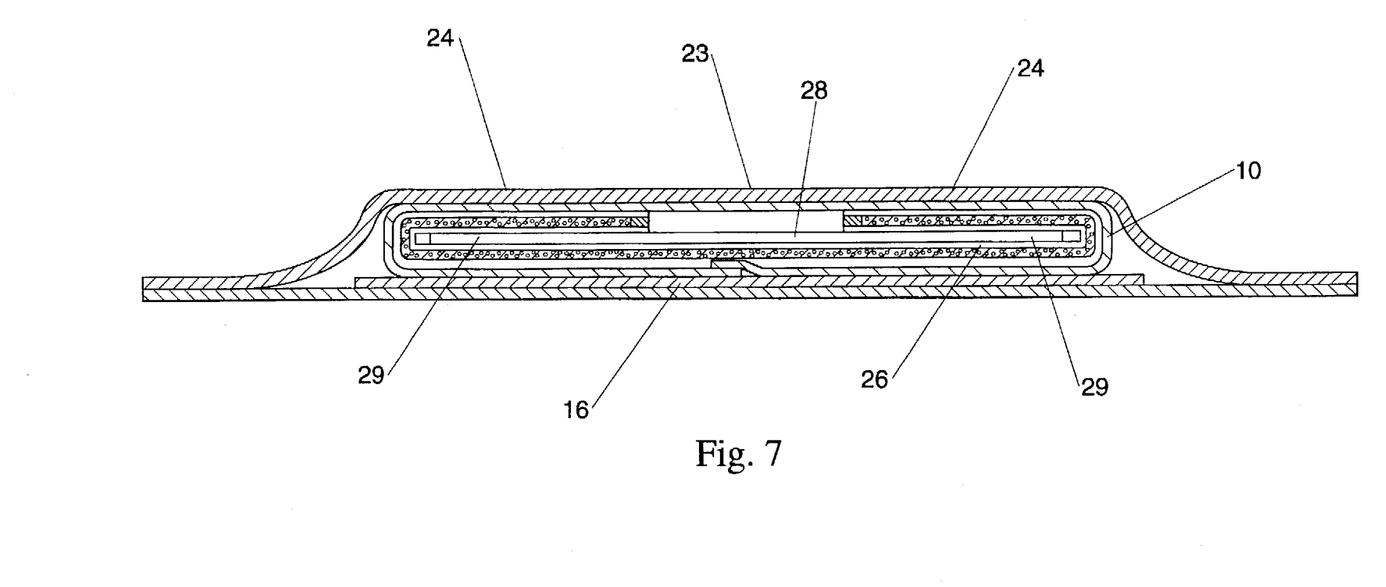
FIG. 7 is a view in section of a further alternative arrangement of a towel according to the present invention, comprising an absorbent element of a type illustrated in FIG. 6.

FIG. 7 illustrates an alternative arrangement of a sanitary towel produced according to the present invention and incorporating an absorbent element of the type illustrated in FIG. 6, having the intermediate layer 10 completely wrapped around the absorbent element and having the lower, stopping layer 16.

In this case, the absorbent element comprises a further upper collection layer 28, positioned such that the longitudinal ends 29 are below the respective longitudinal ends of the layered absorbent structure folded back over the top.

The density of the upper collection layer 28 is preferably greater than that of the upper fibrous layer 26, which is also constituted, for example, by a dry-formed layer of short cellulose fibres.

In general, the density of the fibrous layers forming the absorbent element 6 is preferably between 0.04 g/cm$^3$ and 0.20 g/cm$^3$.

In this case, the central collection zone 23 of the absorbent element is characterized by the presence of the further collection layer 28.

In use, the upper collection layer 28 firstly receives the liquid, in the central collection zone 23, and transmits it quickly to the underlying layers, distributing it at the same time in longitudinal and transverse directions; the liquid can thus reach the longitudinal ends 29 of the upper collection layer positioned below the folded-back ends of the absorbent structure, and from there be absorbed into the layered absorbent structure, passing both upwards and downwards.

An absorbent element 6 to be incorporated in a shaped-type sanitary towel produced according to the present invention can itself be shaped in the same manner as the external contour of the entire sanitary towel 1.

Figure 8:
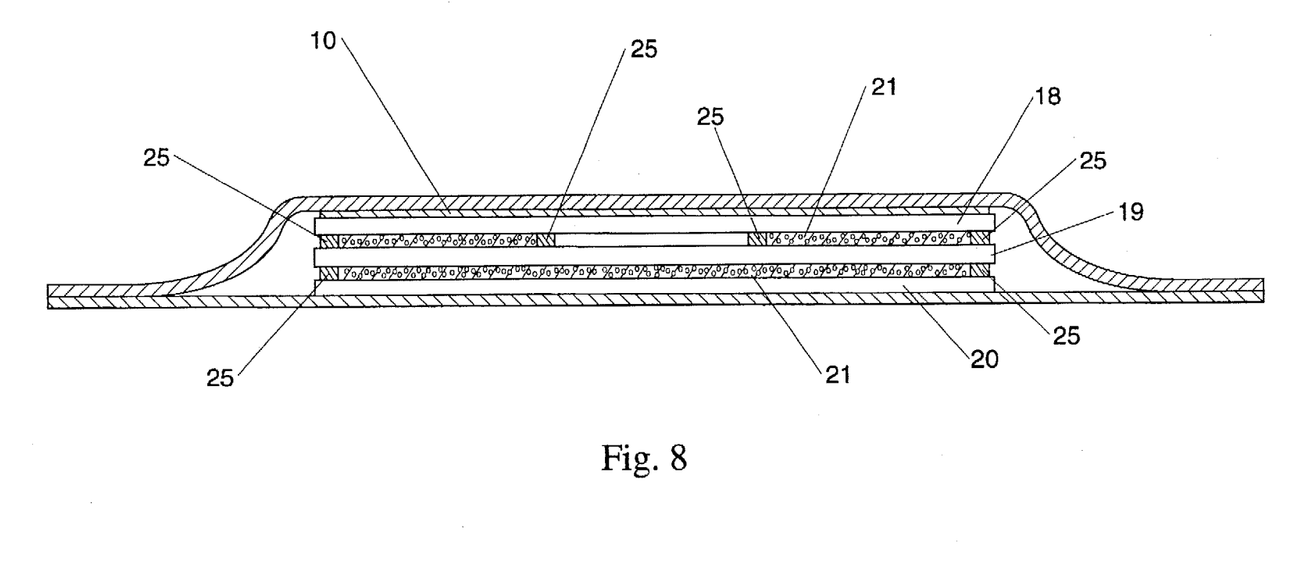
FIG. 8 is a view in section of a further alternative arrangement of a sanitary towel 1 according to the present invention.

FIG. 8 illustrates a first arrangement of a sanitary towel of this type; the absorbent element is of a type similar to that illustrated in FIGS. 2, 4 and 5, but it is composed of a layered absorbent structure formed of superposed fibrous layers 18, 19 and 20 which are wider than the intermediate layers 21 between them and defined by continuous lines of adhesive 25; the intermediate layer 10 is simply superposed on the absorbent structure 6 and preferably has straight and parallel edges and a width which is slightly less than the minimum width of the absorbent element.

In this way, a shaped absorbent element 6 of suitable form can be produced without the cutting line affecting the intermediate layers 21; at the front region 2 and the rear region 3 of the towel, the fibrous layers 18, 19 and 20 extend beyond the continuous line of adhesive 25 which is defined by the intermediate layers 21, providing the structure of the towel with increased consistency and thickness in this zone.

Figure 9:
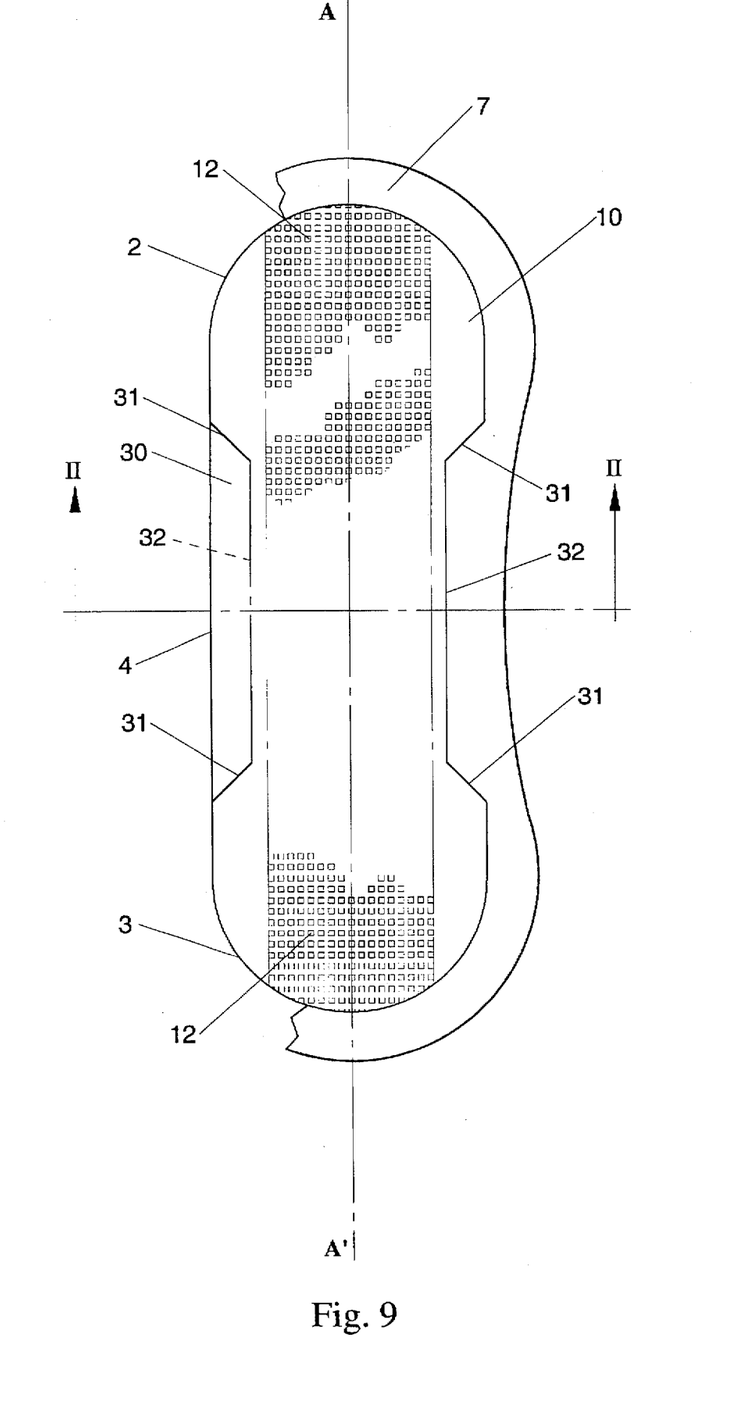
FIG. 9 is a plan view of a further arrangement of the sanitary towel produced according to the present invention, viewed from the side which is to face the user, with the upper layer omitted and part of the structure being incomplete.
Figure 10:
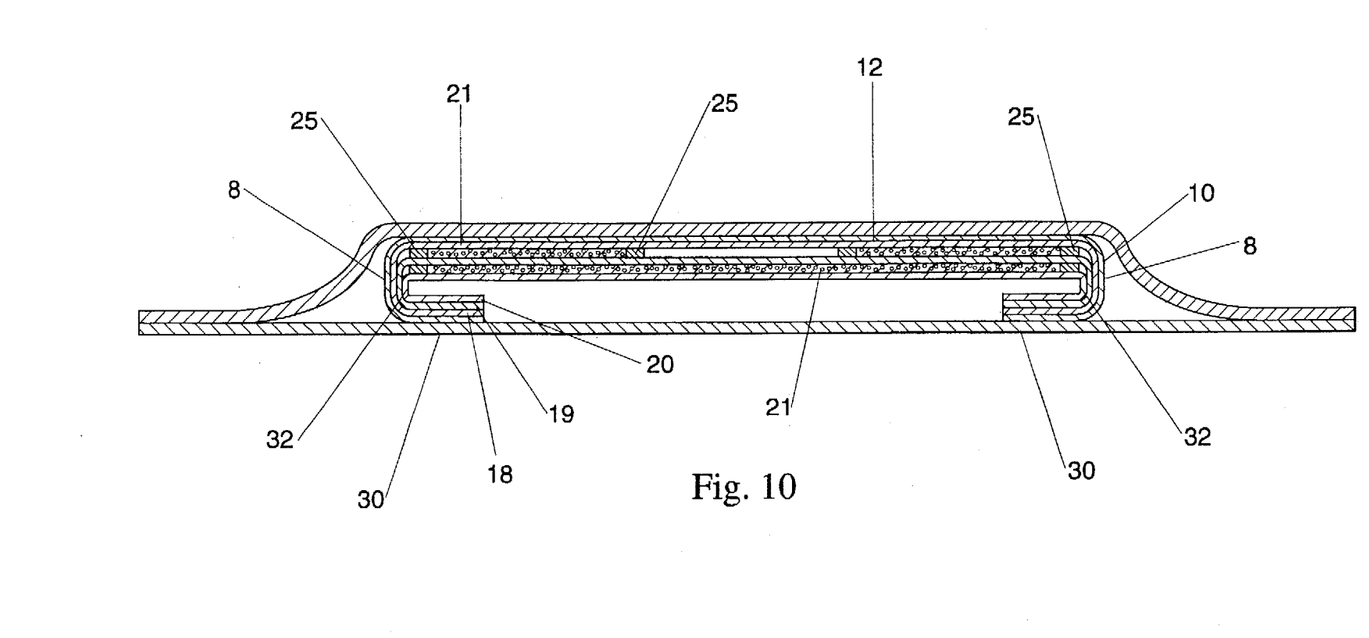
FIG. 10 is a view in section of the towel along the line II—II in FIG. 9.

A preferred embodiment, illustrated in FIGS. 9 and 10, enables a shaped absorbent element to be produced which has an intermediate layer 10 which is to cover the longitudinal edges 8 of the absorbent element 6 and part of the lower surface facing the user's body, at least at the central region 4 of the sanitary towel 1.

The absorbent element is produced from a layered absorbent structure formed of superposed fibrous layers 18, 19 and 20 which are wider than the intermediate layers between them and defined by continuous lines of adhesive 25, on which is superposed an intermediate layer 10 of the same width as the layered absorbent structure, with the substantially permeable zone 12 having a width corresponding to that of the intermediate layers 21.

As illustrated in the plan view in FIG. 9, the portions 30 of the entire structure to be folded back under the structure itself, and formed by the fibrous layers 18, 19 and 20 of the absorbent element 6 and of the longitudinal marginal portions 11 of the superposed intermediate layer 10, are defined by four oblique cuts 31 and by two longitudinal fold lines 32.

FIG. 10 shows the manner in which the portions 30 are folded back under the absorbent structure along the fold lines 31.

A sanitary towel according to the invention, whether it is shaped or not, may also comprise side wings; as is known, when in use, a sanitary towel with side wings is positioned inside the user's underclothing and is, if necessary, secured there whilst the side wings are folded back underneath the underclothing and secured to the external surface thereof in the crotch area.

Figure 11:
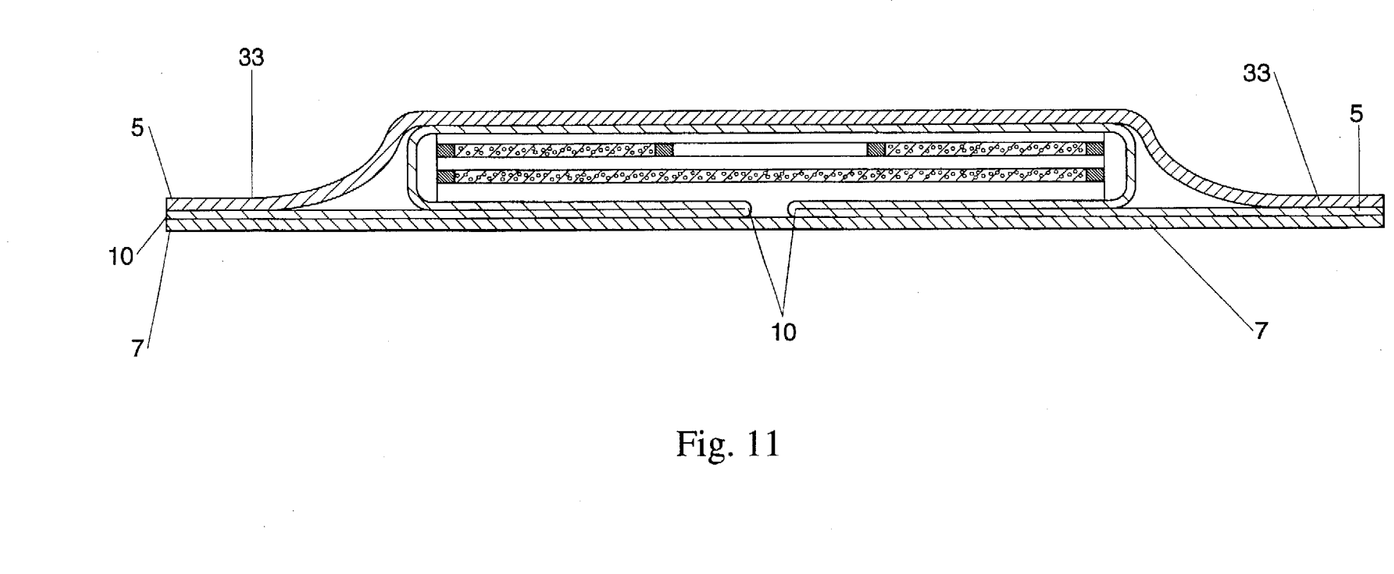
FIG. 11 is a view in section of a sanitary towel with side wings produced according to the present invention.

FIG. 11 shows the manner in which side wings 33 can be produced in accordance with the present invention, a sufficiently wide, suitable intermediate layer 10 being suitably folded in an "omega" shape below the absorbent element 6.

In the arrangement illustrated, each wing 33 is formed by superposing the permeable upper layer 5, the intermediate layer 10 and the impermeable lower layer 7.

A sanitary towel according to the present invention may comprise embossing lines which involve the absorbent element 6 only or the entire structure of the sanitary towel 1, characterized by a substantially longitudinal development.

The object of the embossing lines can be to facilitate the diffusion of the liquid in the longitudinal direction inside the absorbent element 6, creating local densification zones in the structure itself, or also to represent preferred fold lines such that, in use, the sanitary towel adopts a preferred manner of folding, for example in the shape of a "W" such that it can be better adapted to the user's anatomy.

All the individual layers forming the structure of the sanitary towel of the present invention are preferably secured to one another, for example, by means of adhesive.

Naturally, the principle of the invention remaining the same, the details of construction may be varied widely from those described and illustrated without thereby departing from the scope of the present invention.

What is claimed is:

1. A disposable absorbent article having a front region, a rear region, and a central region therebetween, the absorbent article comprising a hydrophilic, liquid pervious topsheet, said topsheet having a body facing surface consisting essentially of a hydrophilic material, a liquid impervious backsheet and an absorbent core disposed between the topsheet and the backsheet, the core having two longitudinal side faces, a body facing surface and a garment facing surface, the body facing surface and the longitudinal side faces of the core being covered by an intermediate layer, wherein the intermediate layer comprises a substantially liquid impervious part overlying the side faces of the core at least in the central region of the absorbent article and a substantially liquid pervious part overlying at least a part of the body facing surface of the core.

2. A disposable absorbent article according to claim 1 wherein an exterior surface of the intermediate layer is hydrophobic at least at the parts of the intermediate layer overlying the side faces of the core.

3. A disposable absorbent article according to claim 1 wherein a barrier layer is located between the backsheet and the core.

4. A disposable absorbent article according to claim 1 wherein the core is formed with at least one longitudinally extended embossed line.

5. A disposable absorbent article according to claim 1 wherein the intermediate layer at least partly overlies the garment facing side of the core.

6. A disposable absorbent article according to claim 5 wherein the intermediate layer fully extends across the body-facing side, the garment facing side, the garment-facing side and the side faces of the core.

7. A disposable absorbent article according to claim 1 wherein the core comprises a first, a second and third fibrous layer, the first fibrous layer being of higher density than the second fibrous layer, the third fibrous layer being of lower density than the first and second fibrous layers.

8. A disposable absorbent article according to claim 7 wherein the third fibrous layer comprises thermobonded fibers.

9. A disposable absorbent article according to claim 1 wherein the intermediate layer has a bulk greater than 5 $cm^3/g$.

10. A disposable absorbent article according to claim 9 wherein the intermediate layer has a bulk greater than 7 $cm^3/g$.

11. A disposable absorbent article according to claim 9 wherein the intermediate layer comprises a laminate of a liquid impervious film and a non-woven material, the non-woven material forming a fibrous wicking layer on the inner surface of the intermediate layer.

12. A disposable absorbent article according to claim 11 wherein the intermediate layer comprises a three-layer structure, comprising a central polyethylene film and two outer polypropylene fibrous layers.

13. A disposable absorbent article according to claim 11 characterized in that the liquid-pervious part of the intermediate layer comprises perforations.

14. A disposable absorbent article according to claim 1 the core comprising two longitudinal sides, characterized in that the core comprises a central, longitudinal acquisition zone and two side zones located between the acquisition zone and the longitudinal sides, the core further comprising an absorbent gelling material, the concentration of absorbent gelling material in the acquisition zone being lower than the concentration of absorbent gelling material in the side zones for transport of liquids in a substantially longitudinal direction of the core.

15. A disposable absorbent article according to claim 14 wherein that the core comprises two fibrous layers between which the absorbent gelling material is comprised, the weight of absorbent gelling material per unit surface area of the fibrous layer being lower in the acquisition zone than in the side zones of the core.

16. A disposable absorbent article according to claim 14 wherein the core comprises at least two fibrous layers in the acquisition zone between which the absorbent gelling material is disposed, the side zones at the body-facing side of the core comprising at least one more fibrous layer and at least one more layer of absorbent gelling material than the acquisition zone.

17. A disposable absorbent article according to claim 16 wherein the core is folded over along its longitudinal sides so that each side zone comprises at least two pair of fibrous layers, a layer of absorbent gelling material being comprised between each pair of fibrous layers.

18. A disposable absorbent article according to claim 16 wherein the fibrous layers are mutually connected by an adhesive along the longitudinal sides of the core and along the sides of the acquisition zone.

19. A disposable absorbent article according to claim 16 wherein a layer of acquisition material is located between the first pair of fibrous layers and the second pair of fibrous layers.

20. A disposable absorbent article according to claim 16 wherein the density of each fibrous layer lies between 0.05 and 0.15 $g/cm^3$.

* * * * *

UNITED STATES PATENT AND TRADEMARK OFFICE
CERTIFICATE OF CORRECTION

PATENT NO. : 5,728,084
DATED : March 17, 1998
INVENTOR(S) : Gianfranco Palumbo et al.

It is certified that error appears in the above-identified patent and that said Letters Patent is hereby corrected as shown below:

Column 2,
Line 13, delete "users" and insert -- user's --.
Line 55, delete "pan" and insert -- part --.

Column 3,
Line 66, delete "from" and insert -- front --.

Column 4,
Line 51, delete "pan" and insert -- part --.

Column 6,
Line 66, delete "babies'nappies" and insert -- babies' nappies --.

Column 7,
Line 8, delete "fluid" and insert -- fluids. --.

Signed and Sealed this

Seventh Day of February, 2006

JON W. DUDAS
*Director of the United States Patent and Trademark Office*